United States Patent [19]

Vincent et al.

[11] 4,288,453

[45] Sep. 8, 1981

[54] DERIVATIVES OF ARYLALKANOIC ACIDS, COMPOSITIONS AND USE

[75] Inventors: Michel Vincent, Bagneux; Jacques Duhault, Chatou; Michelle Boullanger, Marly le Roi; Georges Remond, Versailles, all of France

[73] Assignee: Science Union et Cie, Suresnes, France

[21] Appl. No.: 949,571

[22] Filed: Oct. 10, 1978

[30] Foreign Application Priority Data

Oct. 7, 1977 [FR] France .............................. 77 30186
Apr. 27, 1978 [FR] France .............................. 78 12452

[51] Int. Cl.³ ..................... A61K 31/19; C07C 53/134
[52] U.S. Cl. .................................. 424/317; 562/426; 562/470
[58] Field of Search ................. 562/470, 426; 424/317

[56] References Cited

FOREIGN PATENT DOCUMENTS

2554882 6/1976 Fed. Rep. of Germany ...... 562/470
1121027 7/1968 United Kingdom ................ 562/470

*Primary Examiner*—Henry R. Jiles
*Assistant Examiner*—R. W. Ramsuer
*Attorney, Agent, or Firm*—Gordon W. Hueschen

[57] ABSTRACT

There are now described some novel alpha-[1-aryl-2,2,2-trifluoroethoxy (or-ethylthio)]alkanoic acids that are useful for reducing triglycerides and cholesterol levels in the blood of animals. The percentage reduction in test rats has been observed to be from 20 to 65 for triglycerides and from 15 to 50 for cholesterol. A representative compound of the invention is alpha-(2,2,2-trifluoro-1-phenyl-1-ethoxy)butyric acid. Most of the compounds have an $LD_{50}$ greater than 800 mg/kg, intraperitoneally, in male mice.

A method of use, compositions, and a process for synthesis are also described.

12 Claims, No Drawings

DERIVATIVES OF ARYLALKANOIC ACIDS, COMPOSITIONS AND USE

This invention relates to novel arylalkanoic acids and their derivatives. More precisely this invention relates to arylalkanoic acids and the derivatives thereof, the alkyl chain of which is interrupted by an oxygen or a sulphur atom.

Specifically, it provides the (arylalkyl) alkanoic acids and their derivatives having the formula I

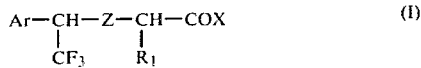

wherein Z is an oxygen or a sulphur atom;

$R_1$ is a lower alkyl radical having from 1 to 5 carbon atoms, lower-alkenyl radical, polyalkenyl radical, lower-cycloalkyl radical, aryl or aryl lower-alkyl radical;

Ar is a mono- or bicyclic aromatic radical, selected from the group consisting of a homocyclic unsubstituted or substituted aromatic radical having from 5 to 7 carbon atoms in each ring and heterocyclic aromatic radical having from 5 to 7 ring atoms in each ring;

and X is a hydroxy, the grouping OM in which M is the monovalent cation of a mineral or organic base, a lower-alkoxy radical, a hydroxy lower-alkoxy radical, a polyhydroxy lower-alkoxy radical, a (di-lower-alkylamino) lower-alkoxy radical, an amino, a lower-alkylamino, a di-lower-alkyl amino, a lower-alkyleneamino, an aryl lower-alkylamino, a N-lower-alkyl N-arylloweralkylamino, a hydroxyamino, a lower-alkoxyamino, a lower-alkylcarbonyloxyamino, a ($R_2$-piperazinyl-1) radical in which $R_2$ is a lower-alkyl, a hydroxylower-alkyl, a lower-alkoxy lower-alkyl or a lower-alkylcarbonyloxy lower-alkyl radical.

This invention also provides the salts of the compounds of formula I. When X is a hydroxy, it may be salified with an organic or inorganic base, preferably a therapeutically-compatible base. When X is a hydroxyamino radical, it may be also salified with an organic or inorganic base, namely a strong base.

Further when Ar is a cyclic aromatic radical bearing a basic substituent, the compounds of formula I may be salified with an organic or inorganic acid to provide the corresponding acid addition salt.

As far as the invention is concerned, the term lower-alkyl for $R_1$, Ar or X is intended to designate a hydrocarbon straight or branched chain having from 1 to 5 carbon atoms such as a methyl, ethyl, n-propyl, iso propyl, sec butyl, tert butyl, neo pentyl, and n-pentyl radical.

The term "lower-alkenyl radical" is intended to designate a hydrocarbon chain having a carbon-carbon double bond and containing from 2 to 6 carbon atoms in straight or branched chain.

Examples of such radicals are vinyl, allyl, methallyl, dimethylallyl, but-2-enyl, but-3-enyl and pent-1-enyl radical.

The term "polyalkenyl radical" is intended to designate a hydrocarbon chain having at least two carbon-carbon double bonds such as a trialkylmethyl, a geranyl, a farnesyl, a linalyl, an octadeca-9,12-dienyl, and an octadeca-3,9,12-trienylradical.

The term "lower-cycloalkylradical" is intended to designate a cyclic saturated chain having from 3 to 7 carbon atoms and which may be substituted with one or two lower-alkyl radicals.

Examples of such radicals are cyclopropyl, cyclobutyl, 2,2-dimethylcyclopropyl, 1-tertbutylcyclopropyl, cyclopentyl, cyclohexyl and 2,6-dimethylcyclohexyl radical.

When $R_1$ is an arylradical, this term is intended to designate an aromatic monocyclic radical which may incorporate one or more heteroatoms selected from the group consisting of oxygen, sulfur, and nitrogen. Examples of such arylradicals are a phenyl, a thienyl, an oxazolyl, a pyrrolyl, a thiadiazolyl or a furyl radical. Preferably this radical has 5 or 6 ring atoms.

The term "aryl lower-alkyl" is intended to designate an aryl radical defined as above-indicated substituted with a hydrocarbon side-chain having from 1 to 6 carbon atoms. Examples of such radicals are benzyl, phenylethyl, β-methyl phenylethyl, phenylisopropyl, thienyl-2-methyl, thienyl-3-methyl, furyl-2-methyl, and pyridyl-4-butyl.

When Ar is a monocyclic aromatic radical, it is preferably a phenylradical or a substituted phenylradical. The term "substituted phenyl" encompasses the compounds having the partial structural formula

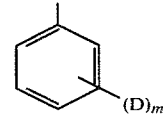

wherein D is a halogen, a lower-alkyl radical, a lower-alkenyl radical, a lower-alkenyloxy radical, a lower-alkynyloxy radical (the radical alkynyl having from 2 to 6 carbon atoms), a loweralkyl thio radical, a hydroxy carbonyl radical, a lower-alkoxycarbonyl radical, a nitro group, an amino, a lower-alkyl carbonylamino, a lower-alkylamino, a diloweralkylamino, an amino sulfonyl, a lower-alkylamino sulfonyl, a dilower-alkylamino sulfonyl, a lower-alkylsulfonyl, an amino carbonyl, a cyano group, a trifluoromethyl, a lower-alkylenedioxy, a lower-alkoxy, a N-piperidinyl, a N-morpholyl, a N-alkylpiperazinyl-1, a phenyl, a phenoxy, a phenylcarbonyl, a substituted phenoxy, and a phenylthioradical.

m is an integer of 1 to 5.

When Ar is a mono- or bicyclic heterocycle, it incorporates as heteroatom, an oxygen, a sulphur, an oxidated sulfur atom, or a nitrogen. Examples of preferred heterocycles are benzofuranyl, thienylfuryl, thiachromanyl, thiachrom-3-enyl, thiachroman dioxide.

When Ar is a bicyclic homocycle it is preferably an α- or β-naphtyl ring, or a benzindenyl ring.

The cation M is that derived from an inorganic base such as alkali metal, for example: sodium, potassium, lithium, ammonium; earth alkaline metals, for example: calcium or strontium, magnesium, aluminium, bismuth, iron (II) and iron (III).

The cation M may also be derived from an organic base, for example: an alkylamine such as dimethylamino ethanol, or tri(hydroxymethyl) aminomethane; an aryl lower-alkylamine such as benzylamine, dibenzyl methylamine, β-methyl phenylethylamine; a quaternary ammonium salt such as choline, betaine; a natural or artificial amino acid such as lysine, valine, ornithine, citrilline, glutamine, serine, β-alanine and the like; a guanidinic base such as arginine, glycocyamine, agmatine and creatinine; a polypeptide such as protamines, clupeine, salmine, caseine; an amino-sugar such as glucosamine, N-methyl glucamine, and mannosamine.

The term lower-alkoxy designates a lower-alkyl oxy radical in which the alkyl moiety has from 1 to 6 carbon atoms in straight or branched chain. Examples of lower-alkoxy are methoxy, ethoxy, isopropoxy, n-butoxy, sec-butyloxy, tert-amyloxy and n-hexyloxy.

When X is a hydroxy lower-alkoxy radical, it may be defined as a lower-alkoxy radical, the alkyl chain of which is substituted with a hydroxy group such as a (β-hydroxyethyl)oxy, a γ-hydroxyisobutyloxy, a 5-hydroxypentyloxy.

When X is a polyhydroxy lower-alkoxy radical, it may include two hydroxyls or more on the alkyl moiety such as an α-glyceryl, a β-glyceryl, an erythrityl, a d-ribityl, a 3,4-dihydroxybutyoxy, a d-glucosyl, a rhamnosyl or a d-xylityl radical.

Further the hydroxy groups may be blocked by such groupings which react with either the vicinal or the non-vicinal diols such as an isopropylidene group, a phenylethylidene or ethylene carbonate. The hydroxy groups may also be combined as an ester or an ether with an acid or an alkylating derivative which may easily be split. Examples of such groupings are the formyloxy, the acetyloxy, the methane sulfonyloxy, the p-pohenesulfonyloxy, the rityl radical or the p-nitrophenyloxy radical.

When X is a dilower-alkylamino alkoxy radical, the alkoxy moiety has from 1 to 6 carbon atoms. Examples of such groupings are diethylamino ethoxy, dipropylamino ethoxy, di iso propylaminobutoxy, dipropylamino propoxy, N-methyl N-butylamino ethoxy. The two lower-alkyl radicals on the nitrogen may form together a cyclic alkylene chain such as a pentamethylene or hexamethylene chain. One of the two lower-alkyl radicals may also be linked to a saturated cyclic structure such as N-ethyl pyrrolidyl-2 or N-methyl piperidyl-2, or to an aromatic structure such as a pyridyl radical.

When X is a mono- or disubstituted amino radical, the substituents on the nitrogen are lower alkyl radicals of 1 to 6 carbon atoms which may be substituted with a hydroxy or an amino group. Examples of such mono- or disubstituted amino groups are ethylamino, diethylamino (β-hydroxyethylamino), β-hydroxypropylamino, di(β-hydroxyethylamino) and methylaminoethylamino.

The two substituents on the nitrogen atom may also form a cyclic structure having from 2 to 6 carbon atoms such as an aziridinyl, azetidinyl, pyrrolidyl, piperidyl, hexamethyleneimino or a 3,3-dimethylpiperidyl radical.

When X is an aryl (lower-alkyl) amino radical, the aryl moiety is a phenyl radical or a phenyl substituted with one or more substituents selected from the group consisting of halogen, trifluoromethyl, trifluoromethoxy, trifluoromethylthio, a loweralkoxy, amino, lower-alkyl lower-acylamino, di(loweralkyl)amino, lower-alkylamino and lower-alkylene dioxy.

Examples of such aryllower-alkylamino radicals are benzylamino, phenylethylamino, phenylpropylamino, β-methylphenylethylamino, 3,4-dimethoxy benzylamino, 2,6-dichlorobenzylamino, 3-trifluoromethylbenzylamino, 2,6-dimethylbenzylamino, 3,4,5-trimethoxybenzylamino, 3,4-methylenedioxy benzylamino, syringylamino, veratrylamino, and p-acetylaminobenzylamino.

When X is a N-alkyl N-(arylalkyl) amino radical, the radical alkyl and arylalkyl are defined as previously indicated. The preferred N-alkyl N-aryl lower-alkyl amino radicals are the N-ethyl N-(3-trifluoromethylbenzyl) amino and N-methyl N-(3-trifluoromethylbenzyl)amino radicals.

Among the compounds of formula I, the following groups are of particular interest.

(a) the compounds of formula $I_A$

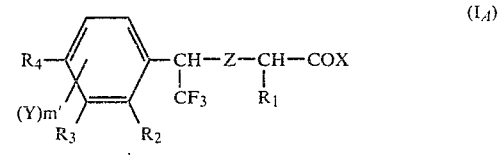

wherein Y is a halogen, a trifluoromethyl, a lower-alkoxy, a lower-alkyl, a hydroxy, a lower-alkyl-sulfonyl or a benzyloxy radical, $R_2$ and $R_3$ and $R_4$ are hydrogen atoms or $R_2$ and $R_3$ and $R_4$ together represent the cyclic remainder of an aromatic ring having from 5 to 7 carbon atoms;

Z is oxygen or sulphur;

X represents a hydroxyl, a lower-alkoxy, an amino or a hydroxylamino group;

and m' is an integer of zero to three.

This class mainly includes the phenyl, indenyl, α or β-naphtyl and benzocycloheptenyl derivatives. The most preferred compounds of formula $I_A$ are:

α-(2,2,2-trifluoro-1-phenylethoxy) propanoic acid, its diastereoisomes, and their enantiomers α-(2,2,2-trifluoro-1-phenylethoxy)butyric acid, its diastereoisomers, and their enantiomers ethyl-α-(2,2,2-trifluoro-1-phenylethoxy)butyrate 4-[a-(b 2,2,2-trifluoro-1-phenylethoxy)butyryl]morpholine ethyl-α-[2,2,2-trifluoro-1-(4-methoxyphenyl)ethoxy]-butyrate 1-[α-(2,2,2-trifluoro-1-phenylethoxy)butyryl]piperidine

[α-(2,2,2-trifluoro-1-phenylethoxy)butyryl]hydroxamic acid ethyl-α-[2,2,2-trifluoro-1-(4-methylphenyl)ethoxy]-butyrate α-[2,2,2-trifluoro-1-(4-chlorophenyl)ethoxy]butyric acid and its diastereoisomers.

(b) the compounds of formula $I_B$

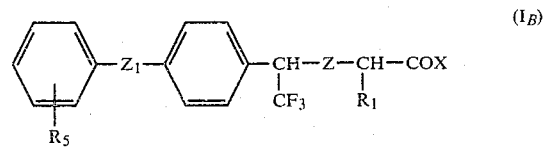

wherein the substituents Z, $R_1$, and X have the above-given definitions, $R_5$ represents hydrogen, a halogen, a trifluoromethyl, a trifluoromethoxy, a trifluoromethylthio radical or a cyano group, and $Z_1$ represents an oxygen, a sulphur atom, a sulfoxide or a sulfonyl group.

(c) the compounds of formula $I_C$

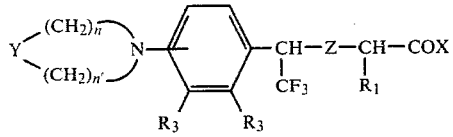 (Ic)

wherein the substituents Z, $R_1$, $R_2$, $R_3$ and X have the above-given definitions:

Y represents a radical —$CH_2$—,

an oxygen or a direct bond between two carbon atoms ($R_6$ being hydrogen or a lower-alkyl radical)

and n and n', the same or different, are 2 or 3.

When the molecules carry a substituent of basic character and namely the compounds of formula $I_C$, they may be salified by adding an organic or inorganic acid, preferably a therapeutically-compatible organic or inorganic acid, such as a hydrochloride, a sulphate, a phosphate, a nitrate, an acetate, a maleate, a fumarate, a nicotinate, a benzoate, an isethionate, or a glucose-1-phosphate. The selection of an anion resides more on the desire to get a compound of greater or lesser solubility in water in the biological fluids or in the oily solvents than in the search of a more specific activity. Further, these compounds may be salified with an acid which possesses some biological activity as, for example: p-chlorophenoxy acetic acid, p-chlorophenoxy isobutyric acid, 5-propylthiazol-2-carboxylic acid, diethylamino acetic acid, di-isopropylacetic acid, or thiazolidinyl-4-carboxylic acid.

The compounds of formula I include in their structures at least two asymmetric carbon atoms and may thus be split into the two diastereoisomeric forms erythro and threo. The splitting may be effected by means of chemical, biological or physical methods.

The erythro or threo diastereoisomers may be further resolved into their optically-active enantiomers. The dextro- or laevorotory isomers are obtained after reaction with a chiral reagent such as an optically-active base, for example: brucine, strychnine, sparteine, or ephedrine. The optically-active enantiomers may also be obtained directly by using a stereospecific way of synthesis.

Using more or less a stereospecific way, the diastereoisomers may be obtined in non-stoichiometric proportions. The mixtures of diastereoisomers or enantiomers in any proportion are within the scope of this invention.

The compounds of formula I and the addition salts thereof are endowed with interesting pharmacological properties. They possess antilipemic and hypocholesterolemic properties.

Due to their pharmacological properties and their low acute toxicity, they found a use in human or veterinary medicine as a drug for treating hyperlipidic overweights, and the simple or mixed hypertriglyceridhaemias. They also may be used as a drug for treating the disturbances of atheroma, alone or together with the usual medicines of the circulatory insufficiency, the arterial blood hypertension and of the arteriopathies of the lower limbs.

Moreover they found a use in the treatment of the vascular diseases resulting from diabetes mellities followed with hyperlipidaemia.

They are used in the form of pharmaceutical compositions containing as active ingredient(s) at least one compound of formula I, or a diastereoisomer thereof, or an optically-active enantiomer thereof in admixture with an inert non-toxic pharmaceutically-compatible carrier or vehicle.

For therapeutic use, the compounds of formula I are presented in any of the pharmaceutical compositions suitable for the administration by parenteral, oral, sublingual, or rectal way.

They may particularly be used as tablets, coated tablets, dragees, soft gelatine capsules, solutions or suspensions to be drunk, the sublingual tablets, the injectible solutions or suspensions packed in ampuls, multi-dosage flasks, auto-injectible syringes; the suppositories, etc.

As appropriate carriers, there may be cited talc, silica, calcium, phosphate, lactose, magnesium, stearate, starches, carboxy methyl, cellulose, for the dry compositions; water or saline solutions for the injectible formulations; cocoa butter or polyethylene glycol stearates for the suppositories. The useful dosology may broadly vary depending upon the age of the patient, the weight of the patient, to the severity of the illness to be treated, and the way of administration. It usually ranges from 100 to 250 mg of active ingredient per unit dosage and from 200 to 1000 mg per day in the patient.

This invention further provides a process for producing the compounds of formula I

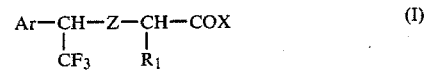 (I)

wherein the substituents Ar, Z, $R_1$, and X have the above-given definitions, wherein an aryltrifluoromethyl ketone or thioketone of the formula II

 (II)

in which Ar has the above-given meanings and Z is an oxygen or a sulphur atom reacted with a reducing agent to provide the corresponding hydrogenated compound of formula III

 (III)

in which Ar and Z have the above-given meanings, which latter is condensed with a metallizing agent to produce the corresponding metal alcoholate, which is further reacted with a α-halo lower-alkyl carboxylic acid of the formula IV

 (IV)

wherein $R_1$ has the previously-given definitions;

Hal is chlorine, bromine or iodine;

and $X_1$ is a hydroxy or a lower-alkoxy radical or a functional derivative of the carboxylic function thereof to produce an (aryl lower-alkyl) alkylcarboxylic acid derivative of the formula V

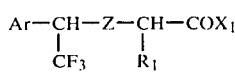 (V)

wherein the substituents Ar, Z, $R_1$, and $X_1$ have the above-given meanings which may, when desired, either be saponified into an acid of the formula I

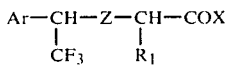 (I)

in which X is a hydroxy and the other substituents have the previously-given definitions, either be converted into a salt by adding an inorganic or organic base, either be transesterified by means of a hydroxy alkanol, a polyhydroxy alkanol, a disubstituted amino alkanol, or a substituted amino alkanol to produce a compound of formula I wherein X is a hydroxy lower-alkyl, a polyhydroxy lower-alkyl, a substituted amino-lower alkyl or a mono-substituted amino lower-alkyl, either be amidified by means of ammonia, a primary amine or a secondary amine to produce a compound of formula I wherein X is an amino group, a lower-alkylamino, a di(lower-alkyl) amino, an aryl lower-alkyl amino, a lower-alkyl (aryl lower-alkyl) amino, or a $R_2$ piperazinyl-1 grouping, or converted into a hydroxyamate by reacting it with hydroxylamine, a 0-loweralkylhydroxylamine or a N-alkylhydroxylamine.

The derivatives of the carboxylic function such as the esters, amides or hydroxamates having the formula I may also be obtained starting from the corresponding carboxylic acid, converting it into a halide, an anhydride or a mixed anhydride and reacting the latter with an alkanol, ammonia, a primary amine, a secondary amine, or a hydroxylamine.

The splitting of the compounds of formula I, which have more than one optically-active carbon atom, may be carried out using chemical or physical methods such as vapor phase chromatography or chromatography on silica gel.

Moreover it is still possible to produce the compounds of formula I starting from racemic raw materials which are resolved in their optically-active isomers using an optically-active reagent.

The compounds of formula I may also be obtained from optically-active precursors and produced as an optically-pure compound, optionally after final purification using the conventional methods of isolation or separation.

The resolution of the enantiomeric compounds of formula I into the laevorotatory and dextrorotatory congener may be performed starting from an enantiomer erythro form or threo form by salification of a compound for which X is a hydroxy with a chiral base as, for example: brucine, quinine, sparteine or 1-p-nitrophenyl-2-dimethylamino-p-copane-1,3-diol.

The compounds of formula I may also be resolved by converting them into an ester of an optically-active alcohol such as 1-mentholcineole, borneol, β-citronellol or β-santatol.

It may be advantageous to produce the compounds of formula I in the optically-active form, starting from an optically-active raw material and more precisely from hydrogenated compounds of formula III

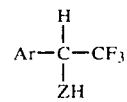 (III)

wherein Z and Ar have the above-given definitions and/or the loweralkylester of a α-haloloweralkylcarboxylic acid of the formula IV

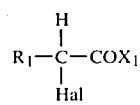 (IV)

in which $R_1$ and Hal have the previously-given definitions and $X_1$ is a lower-alkyl radical.

The compounds of formula III may be conveniently resolved into their optically-active isomers by esterifying them with an optically-active acid such as dibenzoyl, tartaric acid, ditoluyl tartaric acid, abietic acid, d-camphanic acid.

After having the enantiomers separated by using the conventional methods, every ester or thioester is saponified. The compounds of formula III are thus recovered as the optically-active form having the R or S configuration.

These enantiomers of the compounds of formula III may be reacted with a lower-alkyl ester of formula IV as the racemate or in an optically-active form. The reaction between an enantiomer of a compound of formula III and a lower-alkyl ester of formula IV as the racemate gives rise to the formation of a compound of formula I as a mixture of optically-active enantiomers which may further be resolved in the optically-active isomers.

The starting aryl (trifluoromethyl) ketones of formula II are compounds known from the literature. They are obtained from an aryl magnesium halide of the formula Ar Mg X, in which Ar has the above-given definitions and X is a chlorine or a bromine, according to the methods described in J. Org. Chem. 22, 993–994 (1957) or from an aromatic compound as disclosed in the French patent application 2,358,890 (to Science Union et Cie).

The thioketones of formula II (for which Z is a sulphur atom) are obtained from the corresponding ketones using a sulfurizing agent such as phosphorous penta sulphide.

The reduction of the ketones or thioketones of formula II is performed by catalytic hydrogenation using as a catalyst a metal of the platinum family or a mixed hydride. The resulting hydrogenated compound of formula III is obtained in a racemic form. It may be advantageous to carry out the reduction using an optically-active hydride such as an optically-active amine-borane to recover a hydrogenated compound of formula III in an optically-active form.

The metallizing agent is preferably an alcoholate and namely an alkali-metal alcoholate such as those of sodium, potassium, cesium or lithium. The metal alcoholates may also be an aluminium alcoholate. The metal alcoholates are usually produced by reacting a metallic derivative such as butyl lithium, dimisyl sodium, phenyl sodium, potassium tert-amylate lithium (diethylamino hydride), or aluminium isopropylate with a compound of formula III.

The same applies to the compounds of formula III when Z is a sulphur atom.

The condensation between the metal alcoholate of formula III and the lower-alkyl ester of an α-halo alkyl carboxylic acid of formula IV is performed in an inert solvent, preferably a polar solvent such as acetonitrile, tetrahydrofuran, dimethylformamide, dimethylacetamide, dimethylsulfoxide, or hexamethylphosphorotriamide.

The ε-halogenoderivative of formula IV is preferably an α-chloro or an α-bromo derivative. It may also be convenient to use in lieu of a halo derivative, another α-derivative which carries a substituent which may be easily split such as a p-tolysulfonyloxy, a methanesulfonyloxy, an ethanesulfonyloxy, or an amino.

Among the lower-alkyl esters of formula IV, the methyl ester or isopropyl ester are the most preferred.

The saponification of the compounds of formula I (wherein X is a lower alkoxy) may be performed by warming in a basic medium, preferably in an aqueous solvent or in an inert solvent such as ethanol, dioxane, or tetrahydrofuran.

The following examples are merely intended to illustrate the invention. They do not restrict it in any manner. The temperatures are expressed in degrees Centigrade.

EXAMPLE I

Ethyl-α-(2,2,2-trifluoro-1-phenylethoxy)butyrate

STEP A

In a flask, there are successively introduced 200 ml of ethanol and 5.75 g of sodium previously cut into thin slices. After termination of the gas evolution, all the cuttings are dissolved by stirring and a solution of sodium ethanolate is obtained.

The solution of sodium ethanolate is transferred into a three-neck flask under an atmosphere of nitrogen. Then is added thereto 44 g of dl-2,2,2-trifluoro-1-phenylethanol previously dissolved in 200 ml ethanol. The whole mixture is kept under stirring at room temperature for one hour.

The solvent is thereafter evaporated off under reduced pressure, then the solvating ethanol by slight warming at about 60° under reduced pressure. 51.2 g of the sodium alcoholate are thus obtained and used as such for the next step of the synthesis.

STEP B 10.3 g of the sodium-2,2,2-trifluoro-1-phenylethanolate, obtained according to the process of Step A, are transferred into a three-neck flask with 50 ml dimethylformamide. After complete mixing, there is slowly added while cooling with an ice-bath a cooled mixture of 9.4 g ethyl-2-bromobutyrate and 35 ml dimethylformamide. The reaction is strongly exothermic and external cooling is applied so that the temperature of the reaction mixture does not go over 20°. The stirring and the cooling of the mixture are kept for four days.

The solvent is thereafter evaporated off and the dry residue is taken up in a mixture of water and ether. The ethereous phase is separated, washed with water, dried on sodium sulphate, filtered and evaporated to dryness. The dry residue weighs about 11.1 g and substantially consists of ethyl-α-(2,2,2-trifluoro-1-phenylethoxy)butyrate.

This compound is further purified by fractional distillation under reduced pressure. The fraction distilling at 140°-142° under 20 mm is the only fraction which is recovered. The yield amounts to about 43.5% of the theory.

EXAMPLE II

α-(2,2,2-trifluoro-1-phenyl-1-ethoxy)butyric acid 14.8 g of ethyl-α-(2,2,2-trifluoro-1-phenyl-1-ethoxy)-butyrate obtained by Example I is dissolved in 50 ml ethanol. To this solution 28 ml 2 N aqueous solution of sodium hydroxide is added thereto. The mixture is heated to reflux for three hours and the solvent is evaporated off. The aqueous phase is thereafter diluted with water, then extracted three times with ether. The aqueous phases are then made acidic by adding enough hydrochloric acid 6 N. An oily precipitate appears and is extracted with 100 ml ether in three portions. The ethereous phases are separated, washed with water, dried, and evaporated off.

12.6 g of α-(2,2,2-trifluoro-1-phenylethoxy)butyric acid are recovered which are further purified by fractional distillation under very reduced pressure.

11.4 g of a pure compound is obtained. It boils at 122–125./0.01 mm Hg. The yield amounts to 85%.

The resulting acid is a mixture of the two diastereoisomers erythro and threo. It is soluble in the previously-calculated amount of sodium hydroxide in aqueous solution, giving rise to the sodium salt.

| ANALYSIS-$C_{12}H_{13}F_3O_3$ = 262.22 | | |
|---|---|---|
| | C | H % |
| Calculated | 54.96 | 5.00 |
| Found | 55.01 | 4.97 |

EXAMPLE III

Ethyl-α-(2,2,2-trifluoro-1-phenylethoxy)propionate

Using the same procedure as in Example I, Step B, starting from 10.3 g sodium-2,2,2-trifluoro-1-phenylethanolate and 9.4 g ethyl-2-bromopropionate, 6.2 of the title compound is isolated.

Ethyl-α-(2,2,2-trifluoro-1-phenylethoxy)propionate is obtained as a liquid boiling at 140°-142°/20 mm Hg. The yield amounts to 43.5%.

EXAMPLE IV dl-α-(2,2,2-trifluoro-1-phenylethoxy)propionic acid

Using the same procedure as in Example II, starting from 3.9 g ethyl α-(2,2,2-trifluoro-1-phenylethoxy)propionate, the corresponding propionic acid derivative is obtained with a yield of 84%.

The pure compound is an oily solid which melts without clear melting point between 30° and 50°. It dissolves in the stoichiometric amount of sodium hydroxide.

| ANALYSIS-$C_{11}H_{11}F_3O_3$ = 248.21 | | |
|---|---|---|
| | C | H % |
| Calculated | 53.24 | 4.47 |
| Found | 53.56 | 4.49 |

EXAMPLE V

α-[2,2,2-trifluoro-1-(4-chlorophenyl)ethoxy]butyric acid, α-[2,2,2-trifluoro-1-(4-methylphenyl)ethoxy]-butyric acid, and α-[2,2,2-trifluoro-1-(4-methoxyphenyl)ethoxy]butyric acid Using the procedure of Examples I and II, the following compounds have been obtained starting respectively from α,α,α-trifluoro-4-chlorophenylketone from α,α,α-trifluoro(4-methylphenyl) ketone and from α,α,α-trifluoro(4-methoxyphenyl)ketone.

(1) α-[2,2,2-trifluoro-1-(4-chlorophenyl)ethoxy]butyric acid. Boiling point 142°–143°/0.02 mm Hg. This compound is soluble in an aqueous solution of sodium hydroxide.

| ANALYSIS-$C_{12}H_{12}ClF_3O_3$ = 296.67 | | | |
| --- | --- | --- | --- |
| | C | H | Cl % |
| Calculated | 48.58 | 4.08 | 11.96 |
| Found | 48.50 | 4.04 | 11.93 |

(2) α-[2,2,2-trifluoro-1-(4-methylphenyl)ethoxy]butyric acid.
Boiling point: 128–132/0.2 mm Hg.
Ethyl ester boiling point: 178°–82°/0.04 mm Hg.
α-[2,2,2-trifluoro-1-(4-methoxyphenyl)ethoxy]butyric acid.
Boiling point: 140°–155°/0.04 mm Hg.
This compound is insoluble in water but soluble in alkaline solutions.

| ANALYSIS-$C_{13}H_{15}F_3O_4$ = 292.26 | | |
| --- | --- | --- |
| | C | H % |
| Calculated | 53.43 | 5.17 |
| Found | 53.45 | 5.02 |

Its ethyl ester boils at 105°–115°/0.4 mm Hg.

| ANALYSIS-$C_{15}H_{19}F_3O_4$ = 320.31 | | |
| --- | --- | --- |
| | C | H % |
| Calculated | 56.24 | 5.98 |
| Found | 56.22 | 6.02 |

EXAMPLE VI

α-(2,2,2-trifluoro-1-phenylethoxy)butyryl hydroxamic acid (mixture of diastereoisomers)

In a three-neck flask fitted with a stirring device and with a condenser filled with a mixture of lime and sodium hydroxide 3.15 g of hydroxylamine hydrochloride and 65 ml ethanol are introduced. The solution is achieved by slight warming. After returning to room temperature, a solution of sodium ethylate obtained by reacting 1.05 g sodium with 25 ml ethanol is added thereto. The whole mixture is heated to reflux for 30 minutes and then diluted with 50 ml ethanol. The precipitate of sodium chloride is separated and the clear filtrate is slowly added in about 10 minutes with 8.7 g of ethyl-α-[(2,2,2-trifluoro-1-phenyl)ethoxy]butyrate obtained according to the procedure of Example I and a solution of sodium ethanolate produced by reacting 6.98 g sodium with 20 ml ethanol while maintaining the inner temperature at about 0°. The mixture is thereafter kept aside for a night, then evaporated off. The residue consists essentially of the sodium salt of the hydroxamic acid. The residue is taken up in water, extracted with ether, then acidified to pH 1. The aqueous is extracted three times with ether, the etherous phases are separated, dried on sodium sulphate, filtered and evaporated off. The crystalline residue of the hydroxamic acid is further purified by recrystallizing it from n-pentane.

α-(2,2,2-trifluoro-1-phenylethoxy)butyryl hydroxamic acid melts at about 108° (no clear melting point). It is soluble in the previously-calculated amount of sodium hydroxide.

| ANALYSIS-$C_{12}H_{14}F_3NO$ = 277.24 | | | |
| --- | --- | --- | --- |
| | C | H | N % |
| Calculated | 51.99 | 5.08 | 5.06 |
| Found | 91.98 | 5.00 | 4.96 |

EXAMPLE VII

4-[α-(2,2,2-trifluoro-1-phenylethoxy)butyryl]morpholine (mixture of diastereoisomers) in 40 ml isopropyl ether are added to 4.6 g phosphorous pentachloride and 2 ml pyridine. After perfect mixing, the reaction mixture is kept under stirring at room temperature for four hours then heated to reflux for one hour. Excess of reagents are distilled off and 4.97 g of a residue consisting of α-[(2,2,2-trifluoro-1-phenylethoxy)]butyric acid chloride is recovered.

This residue is taken up in 20 ml ether, which is then added to a solution of 2.95 g morpholine in 20 ml ethyl ether. The mixture is kept under stirring for three (3) hours at room temperature.

After the usual purifications, 3.6 g of the morpholide are recovered. The compound is further recrystallized from ethyl ether. It melts at 75° (no clear melting point). 4-[α-(2,2,2-trifluoro-1-phenylethoxy)butyryl]morpholine is insoluble in water but soluble in the common organic solvents.

| ANALYSIS-$C_{16}H_{20}F_3NO_3$ = 331.34 | | | |
| --- | --- | --- | --- |
| | C | H | N % |
| Calculated | 58.01 | 6.01 | 4.23 |
| Found | 58.01 | 5.95 | 4.56 |

EXAMPLE VIII

1-[α-(2,2,2-trifluoro-1-phenylethoxy)butyryl]piperidine (mixture of diastereoisomers).

Using the same procedure as in Example VII and starting from 2.15 g of piperidine, 3 g of the piperidine are obtained. The compound of oily consistency crystallizes slowly. 1-[α-(2,2,2-trifluoro-1-phenylethoxy)butyryl]piperidine melts at about 45° (recrystallized from ethyl ether). This compound is insoluble in water.

| ANALYSIS-$C_{17}H_{22}F_3NO_2$ = 329.96 | | | |
| --- | --- | --- | --- |
| | C | H | N % |
| Calculated | 62.00 | 6.73 | 4.26 |
| Found | 61.70 | 6.81 | 4.33 |

EXAMPLE IX

Ethyl-α-[2,2,2-trifluoro-1-(p-chlorophenyl)ethoxy]butyrate (diastereoisomers α and β).

The mixture of diastereoisomers obtained according to the procedure of Example V has been split into the diastereoisomers α and β preparative vapor phase chromatography using an apparatus Fractovap P (Carlo Erba). This apparatus is fitted with a 2-m-high column in stainless steel with an internal diameter of 1 cm filled with an absorbent sold under the trade name Gas Chrom.F (mesh 45-60) coated with 10% trifluoropylmethyl silicone QF (Dow Corning).

200 η$^1$ of a 20% solution of the mixture of diastereoisomeric esters in methylene chloride are injected under a pressure of 0.4 bar. The fractions sampler allows the separation of the two diastereoisomers named α and β.

After saponification using the procedure of Example II the two acids are obtained:

The diastereoisomeric ester β provides α-[2,2,2-trifluoro-1-(p-chlorophenylethoxy]butyric acid (isomer β) melting at 97° (from ethyl ether). This compound is soluble in the previously-calculated amount of sodium hydroxide.

| ANALYSIS-C$_{12}$H$_{12}$Cl F$_3$O$_3$ = 296.67 | | |
|---|---|---|
| | C | H % |
| Calculated | 48.48 | 4.08 |
| Found | 48.80 | 4.26 |

The diastereoisomeric acid α is obtained in the same experimental conditions. It is further purified by preparative liquid phase chromatography.

EXAMPLE X

Ethyl-α-(2,2,2-trifluoro-1-phenylethoxy)butyrate diastereoisomers α and β.

The splitting of the two diastereoisomers is obtained, starting from the mixture of diastereoisomers obtained at Example I through a preparative vapor phase chromatograph (Fractovap P apparatus, Carlo Erba). The temperature of the oven is heated to 130° and the temperature of the injector is at 200°. The mixture of diastereoisomers (40 mg) is dissolved in 2 ml methylene chloride. The sample collector allows the recovery of the two diastereoisomeric esters.

After saponification, the two diastereoisomeric acids are obtained.

Diastereoisomer α

Melting point 75°-77° (from petroleum ether)

| ANALYSIS-C$_{12}$H$_{13}$F$_3$O$_3$ = 262.22 | | |
|---|---|---|
| | C | H % |
| Calculated | 54.96 | 5.00 |
| Found | 55.10 | 5.11 |

Diastereoisomer β

Melting point 100° (from ethyl ether)

| ANALYSIS-C$_{12}$H$_{13}$F$_3$O$_3$ = 262.22 | | |
|---|---|---|
| | C | H % |
| Calculated | 54.96 | 5.00 |
| Found | 55.01 | 4.93 |

EXAMPLE XI

2-[1-(4-phenoxyphenyl)-2,2,2-trifluoroethoxy]butyric acid (mixture of diastereoisomers)

STEP A 4-fluoro-α,α,α-trifluoroacetophenone

In a three-neck flask, 52.5 g of 4-fluoro-1-bromobenzene are charged with 60 ml ether, then 7.3 g magnesium turnings. The walls of the flask are rinsed with a few ml ether. Small crystals of iodine are added thereto and the mixture is heated to reflux until all the magnesium has reacted with the same. The mixture is left to revert to room temperature, then a solution of 11.4 g trifluoro acetic acid in 15 ml ether is very slowly added in about 20 minutes. The inner temperature is kept at about 20°-30° by external cooling. The mixture is kept aside at room temperature for 15 minutes and then heated to reflux for three hours. The mixture is thereafter kept in a cool place for 12 hours. The cooled mixture is poured on a mixture of crushed ice and chlorhydric acid. The etherous phase is separated. The aqueous phase is extracted twice with 100 ml ether.

The etherous solutions are united, washed with an aqueous saturated solution of sodium bicarbonate, then with water until the washings are neutral, dried-on sodium sulphate, filtered and evaporated off. 82.8 g of 4-fluoro-α,α,α-trifluoroacetophenone are recovered and further purified by fractional distillation.

The pure compound boils at 60°-64°/18 mmHg.

That analytical constant corresponds to that of the literature.

STEP B 4-phenoxy-α,α,α-trifluoroacetophenone 1.92 of 4-fluoro-α,α,α-trifluoroacetophenone and 50 ml dimethylsulfoxide are mixed together and 1.15 g phenol and 1.35 g sodium carbonate are added thereto. The whole mixture is heated at 100° under stirring for seven hours. The mixture is left to revert to room temperature, then poured into 50 ml water. The suspension is extracted three times with 25 ml ether and the etherous phases are united. They are washed with water, dried, filtered and distilled off. 1.3 g 4-phenoxy-α,α,α-trifluoroacetophenone are recovered as a viscous oil.

STEP C (4-phenoxyphenyl)-α,α,α-trifluoroethanol 17.1 g 4-phenoxy-α,α,α-trifluoroacetophenone and 90 ml methanol are added in a flask. The clear solution is cooled to 0° by means of an ice bath and 4.74 g sodiumborohydride are added thereto portion-wise. The external cooling is maintained so that the temperature of the reaction mixture does not increase up to 15°. After one hour of stirring, the mixture is left to revert to spontaneous temperature and kept aside for eight hours. The excess of borohydride is destroyed by adding 1 ml acetic acid, and methanol is distilled off. The residue is taken in ethyl ether and washed with a few ml of water. After evaporation of the solvent, 4-phenoxyphenyl-α,α,α-trifluoroethanol is recovered (yield, 14.5 g) as a white solid melting at 70°. This compound is purified by fractional distillation. The pure fraction boils at 184°-190°/18 mmHg.

STEP D

Sodium salt of 4-phenoxyphenyl-α,α,α-trifluoroethanol

A solution of sodium ethanolate is obtained by reacting 0.575 g sodium with 60 ml ethanol.

6.5 g of 4-phenoxyphenyl-α,α,α-trifluoroethanol are added thereto and the whole mixture is kept under stirring for one hour at room temperature. The solvent is thereafter evaporated off and the residue weighing 7.8 g is used without further purification for the next step of the synthesis.

STEP E

Ethyl-2-[1-(4-phenoxyphenyl)-2,2,2-trifluoroethoxy] butyrate 7.8 g of the sodium salt obtained at Step D are dissolved in 50 ml dimethylformamide and to this solution a solution of 6.8 g ethyl-2-bromobutyrate in 25 ml dimethylformamide is added drop-wise. The reaction medium is kept for 12 hours under stirring at room temperature. The solvent is thereafter distilled off under reduced pressure. 8.57 g of ethyl-2-[1-(4-phenoxyphenyl)-2,2,2-triluoroethoxy]butyrate are recovered as a thick oily product.

| ANALYSIS-$C_{20}H_{21}O_4F_3$ = 382.38 | | | |
|---|---|---|---|
| | C | H | F % |
| Calculated | 62.76 | 5.53 | 14.90 |
| Found | 62.92 | 5.53 | 14.90 | dl-2-[1-(4-phenoxyphenyl)-2,2,2-trifluoroethoxy]-butyric acid (mixture of diastereoisomers)

8.5 g of ethyl-2-[1-(4-phenoxyphenyl)-2,2,2-trifluoroethoxy] butyrate obtained at Step E are suspended in a mixture of 22 ml N aqueous solution of sodium hydroxide and 25 ml ethanol. The reaction mixture is kept under stirring for ten hours. The solvent is thereafter evaporated off. The dry residue is taken up in water and the aqueous solution is extracted twice with ether. The remaining aqueous solution is then made acidic by adding 4 N solution of hydrochloric acid and extracted with ether.

After the usual purification, the solvent is evaporated off allowing the recovery of 5.5 g of 2-[1-(4-phenoxyphenyl)-2,2,2-trifluoroethoxy]butyric acid as a very thick liquid.

This compound is dissolved in the stoichiometric amount of N/10 aqueous sodium hydroxide. After evaporating the water, the sodium salt remains, which is further purified by recrystallizing from ethanol at 50% water.

| ANALYSIS OF THE ACID-$C_{18}H_{17}F_3O_4$ = 354.33 | | |
|---|---|---|
| | C | H % |
| Calculated | 61.02 | 4.83 |
| Found | 61.01 | 5.08 |

EXAMPLE XII dl-2-[1-(4-chlorophenoxyphenyl)-2,2,2-trifluoroethoxy]butyric acid Using the same procedure as in Example XI, but starting from 4-chlorophenol, the following are successively produced:
- 4-chlorophenoxy-$\alpha,\alpha,\alpha$-trifluoroacetophenone as an oil;
- 4-chlorophenoxyphenyl trifluoroethanol as a golden yellow oil;
- the sodium salt of 4-chlorophenoxyphenyl trifluoroethanol;
- ethyl-2-[1-(4-chlorophenoxyphenyl)-2-trifluoroethoxy]butyrate as an oil; and
- dl-2-[1-(4-chlorophenoxyphenyl)-2-trifluoroethoxy]-butyric acid (mixture of diastereoisomers) as an oily product, soluble in dilute sodium hydroxide solutions.

| ANALYSIS-$C_{18}H_{16}Cl F_3O_4$ = 388.77 | | | |
|---|---|---|---|
| | C | H | Cl % |
| Calculated | 55.61 | 4.15 | 9.12 |
| Found | 55.16 | 4.49 | 9.09 |

EXAMPLE XIII dl-2-[1-(phenylthiophenyl)-2-trifluoroethoxy]butyric acid

Using the same procedure as in Example XI, but starting from thiophenol, the following compounds have been produced:
- 4-(phenylthio)-$\alpha,\alpha,\alpha$-trifluoroacetophenone (theoretical yield);
- (phenylthiophenyl)-$\alpha,\alpha,\alpha$-trifluoroethanol (Yield of the reduction 92.5%);
- sodium salt of (phenylthiophenyl)-$\alpha,\alpha,\alpha$-trifluoroethanol;
- ethyl-2-[1-(phenylthiophenyl)-$\alpha$-trifluoroethoxy]butyrate (yield 90%); and
- dl-2-[1-(phenylthiophenyl)-2-trifluoroethoxy]butyric acid (mixture of diastereoisomers) boiling at 180°–186°/0.04 mmHg. It is a viscous oil which does not crystallize.

| ANALYSIS-$C_{18}H_{17}F_3OS$ = 370.39 | | | |
|---|---|---|---|
| | C | H | S % |
| Calculated | 58.37 | 4.63 | 8.66 |
| Found | 58.49 | 4.65 | 8.44 |

EXAMPLE XIV dl-2-[1-(piperidinophenyl)-2-trifluoroethoxy]butyric acid

Using the same procedure as in Example XI, the following are successively produced, starting from piperidine:
- 4-piperidino-$\alpha,\alpha,\alpha$-trifluoroacetophenone;
- 4-piperidinophenyl-$\alpha,\alpha,\alpha$-trifluoroethanol;
- sodium salt of (4-piperidinophenyl)-$\alpha,\alpha,\alpha$-trifluoroethanol;
- ethyl-2-[1-(4-piperidinophenyl)-2-trifluoroethoxy]butyrate; and
- dl-2-[1-(4-piperidinophenyl)-2-trifluoroethoxy]-butyric acid (mixture of diastereoisomers) and its hydrochloride. The hydrochloride is a colorless solid melting at 165°–170° (from ethyl ether). It is freely soluble in water.

| ANALYSIS-$C_{17}H_{22}F_3NO_3ClH$ = 381.63 | | | | |
|---|---|---|---|---|
| | C | H | N | Cl % |
| Calculated | 53.48 | 6.07 | 3.67 | 9.28 |
| Found | 53.45 | 6.20 | 3.69 | 9.14 |

EXAMPLE XV

Using the same procedure as in Example XI, but starting from morpholine, the following are successively produced:
- 4-morpholine-$\alpha,\alpha,\alpha$-trifluoroacetophenone;
- (4-morpholinophenyl)trifluoroethanol;
- sodium salt of (4-morpholinophenyl)trifluoroethanol;
- Ethyl-2-[1-(4-morpholinophenyl)-2-trifluoroethoxy]butyrate; and dl-2-[1-(4-morpholinophenyl)-2-trifluoroethoxy]-butyric acid (mixture of diastereoisomers) and its hydrochloride.

The hydrochloride is a colorless solid melting at 100°–110° after recrystallization from ether. It is soluble in water.

| ANALYSIS-$C_{16}H_{20}F_3NO_4$ = 383.80 | | | | |
|---|---|---|---|---|
| | C | H | N | Cl % |
| Calculated | 50.07 | 5.51 | 3.65 | 9.24 |
| Found | 49.69 | 5.86 | 3.81 | 8.93 |

EXAMPLE XVI 2-(1-phenyl-2-trifluoroethoxy)hexanoic acid

Starting from the sodium salt of phenyl-α,α,α-trifluoroethanol and ethyl-2-bromohexanoate, the following are obtained: ethyl-2-[(1-phenyl-2-trifluoroethoxy)]-hexanoate as a liquid boiling at 95°–100°/0.1 mmHg and dl-2-(1-phenyl-2-trifluoroethoxy)hexanoic acid as a mixture of diastereoisomers. It is a liquid boiling at 130°/0.05 mmHg.

| ANALYSIS-$C_{14}H_{17}F_3O_3$ = 290.28 | | |
|---|---|---|
| | C | H % |
| Calculated | 57.92 | 5.90 |
| Found | 58.02 | 5.88 |

EXAMPLE XVII dl-2-(1-phenyl-2-trifluoroethoxy)phenyl acetic acid

Starting from the sodium salt of phenyl-α,α,α-trifluoroethanol and ethyl-2-bromophenylacetate, the following is produced:

ethyl-2-(1-phenyl-2-trifluoroethoxy)phenylacetate as a liquid boiling at 135°–139°/0.05 mmHg.

| ANALYSIS-$C_{18}H_{17}F_3O_3$ = 338.14 | | |
|---|---|---|
| | C | H |
| Calculated | 63.91 | 5.00 |
| Found | 63.91 | 4.94 | dl-1-[(1-phenyl-2-trifluoroethoxy)]phenylacetic acid as a liquid boiling at 155°/0.05 mmHg. This compound is soluble in the dilute solutions of sodium hydroxide.

| ANALYSIS-$C_{16}H_{13}F_3O_3$ = 310.27 | | |
|---|---|---|
| | C | H % |
| Calculated | 61.93 | 4.22 |
| Found | 61.89 | 4.32 |

EXAMPLE XVIII dl-2-[1-(thienyl-2)-2,2,2-trifluoroethoxy]butyric acid

Starting from thiophene and trifluoroacetic anhydride, (thienyl-2)trifluoromethyl ketone is obtained as a colorless liquid boiling at 67°–70°/20 mmHg.

The reduction by means of sodium borohydride gives (thienyl-2)trifluoroethanol which boils at 85°–87°/20 mmHg. It is converted to the sodium salt and the latter is reacted according to the procedure of Example I with ethyl-2-bromobutyrate.

The resulting ethyl[(thienyl-2)trifluoroethoxy]butyrate is saponified into the [(thienyl-2)trifluoroethoxy]-butyric acid (mixture of diastereoisomers).

This compound is a liquid boiling at 173°/20 mmHg. It is soluble in dilute solutions of sodium hydroxide.

| ANALYSIS-$C_{10}H_{11}F_3O_3S$ = 268.26 | | | |
|---|---|---|---|
| | C | H | S % |
| Calculated | 44.77 | 4.14 | 11.95 |
| Found | 44.62 | 4.26 | 11.87 |

EXAMPLE XIX 2-(1-phenyl-2-trifluoroethoxy)butyric acid anantiomers RR and RS

Starting from 13 of 1-phenyl trifluoroethanol of configuration R[$\alpha_D$] = −12°2 (c = 1% benzene) obtained from the d-camphanate by saponification according to the procedure described by J. Jurczak (synthesis 1977, p. 258) and from 12.4 g ethyl-2-bromobutyrate, ethyl-2-[(R)1-phenyl-2-trifluoroethoxy]butyrate is produced. After alkaline saponification, 2-[(R)-1-phenyl-2-trifluoroethoxy]butyric acid is obtained. This acid is reacted with thienyl chloride to produce the acid chloride, then contacted with a solution of 1-menthol in pyridine, giving rise to the production of the 1-menthyl esters.

The enantiomeric esters are separated by chromatography on silica (Apparatus Waters) and elution with a mixture of cyclohexane and benzene (70/30). The fractions are collected and evaporated off. By evaporation, one of the epimers crystallizes. It is separated and further recrystallized. The pure epimer melts at 79°.

The other epimer is obtained in a substantially pure state from the mother-liquors.

The two 1-menthyl esters are saponified and the resulting epimeric acids of configuration RR and RS are obtained.

EXAMPLE XX 2-(1-phenyl-2-trifluoroethoxy)butyric acids of configuration SR and SS Using the same procedure as in Example XIX, but starting from 15.4 g of 1-phenyl-trifluoroethanol of configuration S[$\alpha_D$] = +12.9° (c = 1% benzene), 2-[(S)-1-phenyl-2-trifluoroethoxy]butyric acid is obtained. It is further converted, along the same procedure, into the 1-menthyl esters, starting from laevo-rotatory menthol.

1.82 g of 1-menthyl esters (mixture of epimers) are chromatographed on a column of silica and eluted with a mixture of benzene-cyclohexane. The eluates are collected and evaporated off. 0.3 g of an unresolved mixture, 0.4 g of the 1-menthyl ester (epimer α), and 0.25 g of the other 1-menthyl ester (epimer β), are successively obtained.

On TLC the migrations of the two epimers are:
epimer α $R_f$ = 0.09
epimer β $R_f$ = 0.13
By vapoic phase chromatography, the retention period on CAR column of 2 mm diameter, at a temperature of 200° and at a pressure of 3.5 bar of nitrogen are:
epimer α = 156 seconds
epimer β = 192 seconds
The saponification in alkaline medium of each epimer allows the production of 2-(1-phenyl-2-trifluoroethoxy)butyric acid of configuration SR and SS:

epimer S αMP=46°–47°
epimer S βMP=48°

EXAMPLE XXI

Dl-2-[(naphtyl-1)-2,2,2-trifluoroethoxy]butyric acid

Using the same procedure as in Example XI, but starting from 11 g bromonaphtalene, there are successively produced:
α,α,α-trifluoroethyl naphtyl ketone;
α,α,α-trifluoro naphtyl ethanol;
ethyl-2-[(naphtyl-1)-2,2,2-trifluoroethoxy]butyrate (mixture of diastereoisomers); and 2-[(naphtyl-1)-2,2,2-trifluoroethoxy]butyric acid (mixture of diastereoisomers) as a liquid boiling at 155°/0.05 mmHg.

This compound is soluble in the previously-calculated amount of sodium hydroxide. The acqueous solution has a pH value of 7–8.

| ANALYSIS-$C_{16}H_{15}F_3O_3$ = 312.30 | | |
| --- | --- | --- |
| | C | H % |
| Calculated | 61.54 | 4.84 |
| Found | 61.21 | 4.90 |

EXAMPLE XXII dl-2-[(naphtyl-2)-2,2,2-trifluoroethoxy]butyric acid

Using the same procedure as in Example XI, but starting from 2-bromonaphtalene (10.5 g), there are successively produced:
β-(2,2,2-trifluoroethyl)naphtyl ketone;
β-(2,2,2-trifluoro)naphtylethanol;
ethyl-2-[1-(naphtyl-2)-2,2,2-trifluoroethoxy]butyrate; and
dl-2-[1-(naphtyl-2)-2,2,2-trifluoroethoxy]butyric acid (mixture of diastereoisomers).

Melting point: 80° (from pentane) This compound is soluble in the previously-calculated amount of sodium hydroxide.

| ANALYSIS-$C_{16}H_{15}F_3O_3$ = 312.30 | | |
| --- | --- | --- |
| | C | H % |
| Calculated | 61.54 | 4.84 |
| Found | 61.48 | 4.90 |

EXAMPLE XXIII dl-2-[1-(N-methylpyrrolyl-2)-2,2,2-trifluoroethoxy]-butyric acid Using the same procedure as in Example I and in Example II, but starting from (N-methylpyrrolyl-2)trifluoromethyl ketone obtained according to the process disclosed in the Belgian patent No. 854,908, there are successively produced:
(N-methylpyrrolyl-2)-α,α,α-trifluoroethanol as an oil;
the sodium salt of (N-methylpyrrolyl-2)-α,α,α-trifluoroethanol;
ethyl-2-[1-(N-methylpyrrolyl-2)-2,2,2-trifluoroethoxy]butyrate as a liquid; and
dl-2-[1-(N-methylpyrrolyl-2)-2,2,2-trifluoroethoxy]acid (mixture of diastereoisomers), melting at 156°–157°.

| ANALYSIS-$C_{11}H_{14}F_3NO_3$ = 265.11 | | | |
| --- | --- | --- | --- |
| | C | H | N % |
| Calculated | 49.79 | 5.32 | 5.28 |
| Found | 49.98 | 5.27 | 5.12 |

EXAMPLE XXIV dl-2-[[4-(1-hexamethyleneimino)phenyl]-2,2,2-trifluoroethoxy] butyric acid (mixture of diastereoisomers)

Using the same procedure as in Example XI, but starting from hexamethyleneimine, there are produced:
4-(hexamethyleneimino)-1)-α,α,α-trifluoroacetophenone;
4-[(hexamethyleneimino-1)phenyl]-α,α,α-trifluoroethanol;
the sodium salt of [4-(hexamethyleneimino-1)phenyl]-α,α,α-trifluroethanol;
ethyl-2-[1-4-(hexamethyleneimino-1)phenyl-α,α,α-trifluoroethoxy]butyrate; and
2-[1-[4-(hexamethyleneimino-1)phenyl-2,2,2-trifluoroethoxy]] butyric acid (mixture of diastereoisomers) which melts at 95°–105°.

| ANALYSIS-$C_{18}H_{24}F_3NO_3$ = 359.39 | | | |
| --- | --- | --- | --- |
| | C | H | N % |
| Calculated | 60.16 | 6.73 | 3.90 |
| Found | 59.61 | 6.65 | 4.16 |

This compound is soluble in the dilute aqueous solutions of sodium hydroxide, but insoluble in diluted hydrochloric acid.

EXAMPLE XXV dl-2-[[4-(heptamethyleneimino-1)phenyl-2,2,2-trifluoroethoxy)] butyric acid Using the same procedure as in Example XI, and starting from heptamethyleneimine, there are obtained:
[4-(heptamethyleneimino-1)phenyl]-α,α,α-trifluoroethanol;
the sodium salt of [(4-heptamethyleneimino-1)phenyl]-α,α,α-trifluoroethanol;
ethyl-2-[[1-(4-heptamethyleneimino-1)phenyl]-2,2,2-trifluoroethoxy]butyrate; and
dl-2-[[1-4-heptamethyleneimino-1)phenyl]-2,2,2-trifluoroethoxy]butyric acid (mixture of diastereoisomers).

This compound melts at 110°–125°. It is soluble in the aqueous solutions of sodium hydroxide, but insoluble in hydrochloric acid.

| ANALYSIS-$C_{19}H_{26}F_3NO_3$ = 373.42 | | | |
| --- | --- | --- | --- |
| | C | H | N % |
| Calculated | 61.11 | 7.02 | 3.75 |
| Found | 60.74 | 6.91 | 3.77 |

EXAMPLE XXVI

Tablets containing 0.125 g of dl-2-[1-p-chlorophenyl-2,2,2-trifluoroethoxy]butyric acid per unit dosage

| | |
| --- | --- |
| dl-2-[1-(p-chlorophenyl)-2,2,2-trifluoroethoxy]butyric acid | 1250 g |
| Cornstarch | 900 g |

-continued

| | |
|---|---|
| Calcium phosphate | 850 g |
| Colloidal silica | 250 g |
| Magnesium stearate | 45 g |
| Talc | 375 g |
| Titanium Oxide | 15 g |
| Beet sugar | 1000 g |
| Ethyl cellulose | 40 g |
| Polyethyleneglycol sorbate | 50 g |
| Polyvinyl pyrrolidone | 13 g | for 10,000 tablets, each weighing about .5g.

EXAMPLE XXVII

Pharmacological study of the compounds of Formula I:

(a) Acute toxicity

The acute toxicity of these compounds has been determined on batches of male mice (strain CD) weighing about 20 g. They received the compounds to be tested at increasing doses either intraperitoneally or orally.

The animals are kept under survey for eight days. The deaths when present are numbered.

The average lethal dosage is graphically calculated according to the method of Litchfield and Wilcoxon.

dl-2-[1-(p-chlorophenylethoxy)-2,2,2-trifluoroethoxy] butyric acid has a mean lethal dose (LD$_{50}$) of about 400 mg/kg intraperitoneally. All the other compounds have a LD$_{50}$ intraperitoneally higher than 800 mg/kg and orally higher than 1000 mg/kg.

(b) Determination of the hypolipemic activity

The hypolipemic activity of the compounds of formula I has been determined on batches of male rats (Sprague-Dawley Strain) fed ad libitum with a diet enriched in lipids and containing 10% pork fat. After four days of such feeding, the animals which receive at the same time the compounds to be tested at dosages ranging from 5 to 15 mg/kg per oral dose, are sacrificed two hours after the administration of the compound to be tested. The blood is sampled after having the animals beheaded. A batch of controls is only fed with the hyperlipidic regimen and received merely the solvent.

Another batch of controls receives a normal diet.

The triglycerides in the blood of the rats is determined according to the method of Van Handel and Silversmit, Ann. Biol. Chim. 53, 7 (1965), and the blood cholesterol is dosed using the method adapted to the Technicon Autoanalyser by Levine (Symposium Technicon 1967, 1, 25).

Depending on the compounds and the administered doses, the triglyceride blood content in the treated animal is decreased from 20 to 65% and the cholesterol blood content is decreased from 15 to 40% in comparison to the controls.

(c) Determination of the hypocholesterolemizing activity

Batches of male rats (Sprague-Dowley) are fed with a hypercholesterolemizing regimen containing 2% cholesterol for four days. At the same time the rats received orally the compounds to be tested at doses ranging from 5 to 25 mg/kg.

The fifth day, two hours after the last administration of the tested compounds, the animals are sacrificed and their blood is sampled.

The blood contents in triglycerides and in cholesterol are determined according to the above-cited methods.

Depending upon the administered doses and the nature of the compounds, the decrease of the triglycerides in the blood ranged from 25 to 45% and the decrease of the cholesterol in the blood ranged from 30 to 50% in comparison with the batches or rats which received only the enriched food.

What we claim is:

1. The (Aryl alkyl) alkanoic acids of the formula

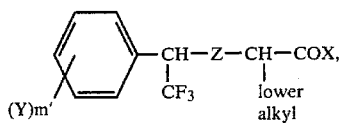

including the diastereoisomers and enantiomers thereof, wherein Z is oxygen or sulphur; lower-alkyl is 1 to 5 carbon atoms, inclusive; Y is halogen, trifluoromethyl, or lower-alkyl; m' is zero or number from one to three, inclusive;

and X is hydroxy, or the grouping OM in which M is the monovalent cation of a mineral base.

2. A compound of claim 1, wherein lower-alkyl is ethyl.

3. The β-diastereoisomers of the compounds of claim 1.

4. A compound of claim 1, which is alpha-(2,2,2-trifluoro-1-phenyl-1-ethoxy)butyric acid.

5. The method of claim 1, wherein the compound administered is alpha-(2,2,2-trifluoro-1-phenyl-1-ethoxy)butyric acid.

6. The pharmaceutical composition of claim 1, wherein the active ingredient is alpha-(2,2,2-trifluoro-1-phenyl-1-ethoxy)butyric acid.

7. The pharmaceutical compositions containing as active ingredient, in effective amount for hypolipemic or hypocholesterolemic action, at least one compound of claim 1 or a salt thereof in admixture with an inert non-toxic pharmaceutical carrier or vehicle.

8. A pharmaceutical composition according to claim 7 wherein the amount of a compound of claim 1 ranges from 100 to 250 mg per unit dosage.

9. A method for treating hyperlipidemia in a patient suffering from high blood content in triglycerides which consists in administering to said patients a safe but effective amount of a compound of claim 1 or a salt thereof for such purpose.

10. The method of claim 9 wherein the safe but effective amount to reduce the triglycerides content in the blood ranges from 200 to 1000 mg per day in the patient.

11. A method for treating hypercholesterolemia in a patient suffering from high blood content in cholesterol which consists in administering to said patient a safe but effective dosage of a compound of claim 1 or a salt thereof for such purpose.

12. The method of claim 11 wherein the safe amount of a compound of claim 1 or a salt thereof effective for reducing high blood content in cholesterol ranges from 200 to 1000 mg per day in the patient.

* * * * *